United States Patent
Wei et al.

(10) Patent No.: US 11,344,188 B1
(45) Date of Patent: May 31, 2022

(54) ACTIVELY BENDABLE SHEATH FOR DELIVERING MEDICAL INSTRUMENT THERETHROUGH AND METHOD THEREOF

(71) Applicant: OTU Medical Inc., Union City, CA (US)

(72) Inventors: Xibo Wei, Hayward, CA (US); Geping Liu, San Jose, CA (US)

(73) Assignee: OTU Medical Inc., Union City, CA (US)

( * ) Notice: Subject to any disclaimer, the term of this patent is extended or adjusted under 35 U.S.C. 154(b) by 0 days.

(21) Appl. No.: 17/303,490

(22) Filed: May 30, 2021

(51) Int. Cl.
*A61B 1/018* (2006.01)
*A61B 1/005* (2006.01)
*A61B 1/307* (2006.01)
*A61M 25/01* (2006.01)
*A61B 1/00* (2006.01)

(52) U.S. Cl.
CPC ............ *A61B 1/018* (2013.01); *A61B 1/0057* (2013.01); *A61B 1/00135* (2013.01); *A61B 1/00154* (2013.01); *A61M 25/0147* (2013.01); *A61B 1/307* (2013.01)

(58) Field of Classification Search
USPC ........................................................ 600/114
See application file for complete search history.

(56) References Cited

U.S. PATENT DOCUMENTS

| | | | | | |
|---|---|---|---|---|---|
| 3,557,780 | A | * | 1/1971 | Sato ..................... | A61B 1/0055 600/141 |
| 4,655,257 | A | * | 4/1987 | Iwashita .............. | A61B 1/0052 138/120 |
| 4,905,666 | A | * | 3/1990 | Fukuda ................ | A61B 1/0052 600/146 |
| 5,199,950 | A | * | 4/1993 | Schmitt ............ | A61M 25/0144 600/585 |
| 5,325,845 | A | * | 7/1994 | Adair ................... | A61B 1/0055 600/114 |
| 5,807,239 | A | * | 9/1998 | DiBernardo ....... | A61B 1/00135 600/114 |
| 5,938,588 | A | * | 8/1999 | Grabover ............. | A61B 1/0057 600/150 |
| 6,599,265 | B2 | * | 7/2003 | Bon .................. | A61M 25/0136 604/95.01 |
| 2001/0037084 | A1 | * | 11/2001 | Nardeo ............. | A61M 25/0138 604/95.04 |
| 2002/0017515 | A1 | * | 2/2002 | Obata .................. | A61B 1/0055 219/137 R |
| 2007/0244356 | A1 | * | 10/2007 | Carrillo ................. | A61B 1/018 600/107 |

(Continued)

Primary Examiner — John P Leubecker
(74) Attorney, Agent, or Firm — George Guosheng Wang; United States Research and Patent Firm

(57) ABSTRACT

An actively bendable sheath such as ureteral access sheath (UAS) and a method for delivering a medical instrument (e.g. a ureteroscope) therethrough are disclosed. The sheath's tubular wall includes a deflectable or bendable segment at or adjacent to the distal sheath end. Two pull/control wires are slidably disposed within two separate dedicated channels/lumens and attached to points distally beyond the deflectable segment. The bendable segment may be passively bended by force from a bending medical instrument within it or by the force of a surgeon pulling one of the two pull/control wires.

18 Claims, 16 Drawing Sheets

(56) References Cited

U.S. PATENT DOCUMENTS

| | | | |
|---|---|---|---|
| 2008/0255422 A1* | 10/2008 | Kondoh | A61B 17/3478 600/141 |
| 2008/0262301 A1* | 10/2008 | Gibbons | A61B 1/01 600/114 |
| 2009/0062606 A1* | 3/2009 | Ueda | A61B 1/0052 600/114 |
| 2011/0105844 A1* | 5/2011 | Sullivan | A61B 1/0055 600/149 |
| 2012/0053415 A1* | 3/2012 | Bunch | A61B 1/00154 600/121 |
| 2013/0144125 A1* | 6/2013 | Konstorum | A61B 1/00066 600/131 |
| 2015/0057610 A1* | 2/2015 | Osypka | A61M 25/0136 604/95.04 |
| 2015/0133959 A1* | 5/2015 | Kato | A61M 25/0147 606/130 |

\* cited by examiner

ACTIVELY BENDABLE SHEATH FOR DELIVERING MEDICAL INSTRUMENT THERETHROUGH AND METHOD THEREOF

FIELD OF THE INVENTION

The present invention generally relates to an actively bendable sheath for delivering a medical instrument therethrough and method thereof. Although the invention will be illustrated, explained, and exemplified by actively bendable ureteral access sheaths for placing an ureteroscope in a urinary tract, it should be appreciated that the present invention can also be applied to access sheaths for other medical devices such as an endoscope, a hysteroscope, a sigmoidoscope, a bronchoscope, a trocar, a guidewire, or an interventional catheter in various vessels (e.g. vascular, biliary, etc.).

BACKGROUND OF THE INVENTION

Surgical access devices typically include a sheath having an outside diameter and an inside diameter. An obturator or dilator is inserted into the sheath to facilitate introduction of the sheath into the body conduit. Once the sheath is positioned, the obturator is removed leaving a working channel for surgical instrumentation.

For example, in the field of urology, a ureteral access sheath (UAS) has been provided in the form of an elongate tube having an axis extending between a proximal end and a distal end. The diameter of the tube is generally constant, ranging between 10F and 16F in outer diameter, except for a reduced diameter segment at the distal end.

A typical UAS also includes a dilator and a sheath. The dilator is placed within the sheath, and the dilator and sheath in combination is advanced through the urethra, through the bladder, and to the ureter. The dilator is then withdrawn, leaving the sheath in place. A medical instrument such as a ureteroscope is then advanced through the sheath to access the ureter. A ureteroscope is configured for examining the inside of the urinary tract, a procedure called ureteroscopy.

Therefore, a UAS can create an access channel from the external meatus to a location within the ureter of a patient to perform any surgical procedures within the ureter and/or kidney. With an established channel to the ureter, a surgeon is able to insert and to withdraw a ureteroscope or other instrument more rapidly and with limited trauma to a patient's urinary system. The use of a UAS during ureteroscopy has been beneficial on many levels: decreased cost of the procedure, better ability to clear stones, and less overall trauma to the ureter.

However, a problem of the conventional UAS is that it does not have enough bending flexibility to reach renal calyces. Another problem of the conventional UAS is that, without pulling the UAS back into the ureter, the tip of an ureteroscope cannot navigate to evaluate the lower pole.

Advantageously, the present invention provides an actively bendable sheath that can overcome the aforementioned problems.

SUMMARY OF THE INVENTION

One aspect of the present invention provides an actively bendable sheath for delivering a medical instrument therethrough. The sheath includes a proximal sheath end, a distal sheath end, and an intermediate sheath region disposed between the proximal sheath end and the distal sheath end. A sheath lumen is defined by a tubular wall extending from the proximal sheath end to the distal sheath end and is configured for the medical instrument to pass through it ("delivering"). The tubular wall comprises a deflectable or bendable segment at or adjacent to the distal sheath end. A first pull/control wire is slidably disposed within a first pull wire channel/lumen that is connected to, and extended along, the tubular wall of the sheath, and a distal end of the first pull wire is affixed to a first attachment point in the first pull wire channel. A second pull/control wire is slidably disposed within a second pull wire channel/lumen that is connected to, and extended along, the tubular wall of the sheath, and a distal end of the second pull/control wire is affixed to a second attachment point in the second pull wire channel. The first attachment point and the second attachment point are located distally beyond at least a portion of the deflectable segment.

Another aspect of the present invention provides a method for delivering a medical instrument into human body, comprising:

(i) providing an actively bendable sheath comprising a proximal sheath end; a distal sheath end; an intermediate sheath region disposed between the proximal sheath end and the distal sheath end; a sheath lumen defined by a tubular wall extending from the proximal sheath end to the distal sheath end, and configured for the medical instrument to pass through it ("delivering"), the tubular wall comprising a deflectable or bendable segment at or adjacent to the distal sheath end; a first pull wire slidably disposed within a first pull wire channel/lumen that is connected to, and extended along, the tubular wall of the sheath, wherein a distal end of the first pull wire is affixed to a first attachment point in the first pull wire channel; and a second pull wire slidably disposed within a second pull wire channel/lumen that is connected to, and extended along, the tubular wall of the sheath, wherein a distal end of the second pull wire is affixed to a second attachment point in the second pull wire channel; wherein the first attachment point and the second attachment point are located distally beyond at least a portion of the deflectable segment;

(ii) inserting the actively bendable sheath into human body;

(iii) pulling the first pull wire or the first pull wire to bend the deflectable segment;

(iv) locking the deflectable segment at the bent position; and (v) repeatedly delivering the medical instrument through the sheath lumen.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The present invention is illustrated by way of example, and not by way of limitation, in the figures of the accompanying drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale. Well-known structures and devices are shown in simplified form, omitted, or merely suggested, in order to avoid unnecessarily obscuring the present invention.

DETAILED DESCRIPTION OF THE PREFERRED EMBODIMENT

In the following description, for the purposes of explanation, numerous specific details are set forth in order to provide a thorough understanding of the present invention. It is apparent, however, to one skilled in the art that the present invention may be practiced without these specific details or with an equivalent arrangement.

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

It is also to be understood that the terminology used herein is for the purpose of describing particular embodiments only and is not intended to limit the scope of the invention. For example, when an element is referred to as being "on", "connected to", or "coupled to" another element, it can be directly on, connected or coupled to the other element or intervening elements may be present. In contrast, when an element is referred to as being "directly on", "directly connected to", or "directly coupled to" another element, there are no intervening elements present.

Throughout the specification and claims, the following terms take the meanings explicitly associated herein, unless the context clearly dictates otherwise. The phrase "in one embodiment" does not necessarily refer to the same embodiment, although it may. Furthermore, the phrase "in another embodiment" does not necessarily refer to a different embodiment, although it may. Thus, as described below, various embodiments of the invention may be readily combined without departing from the scope or spirit of the invention.

In addition, as used herein, the term "or" is an inclusive "or" operator and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

Figure 1:
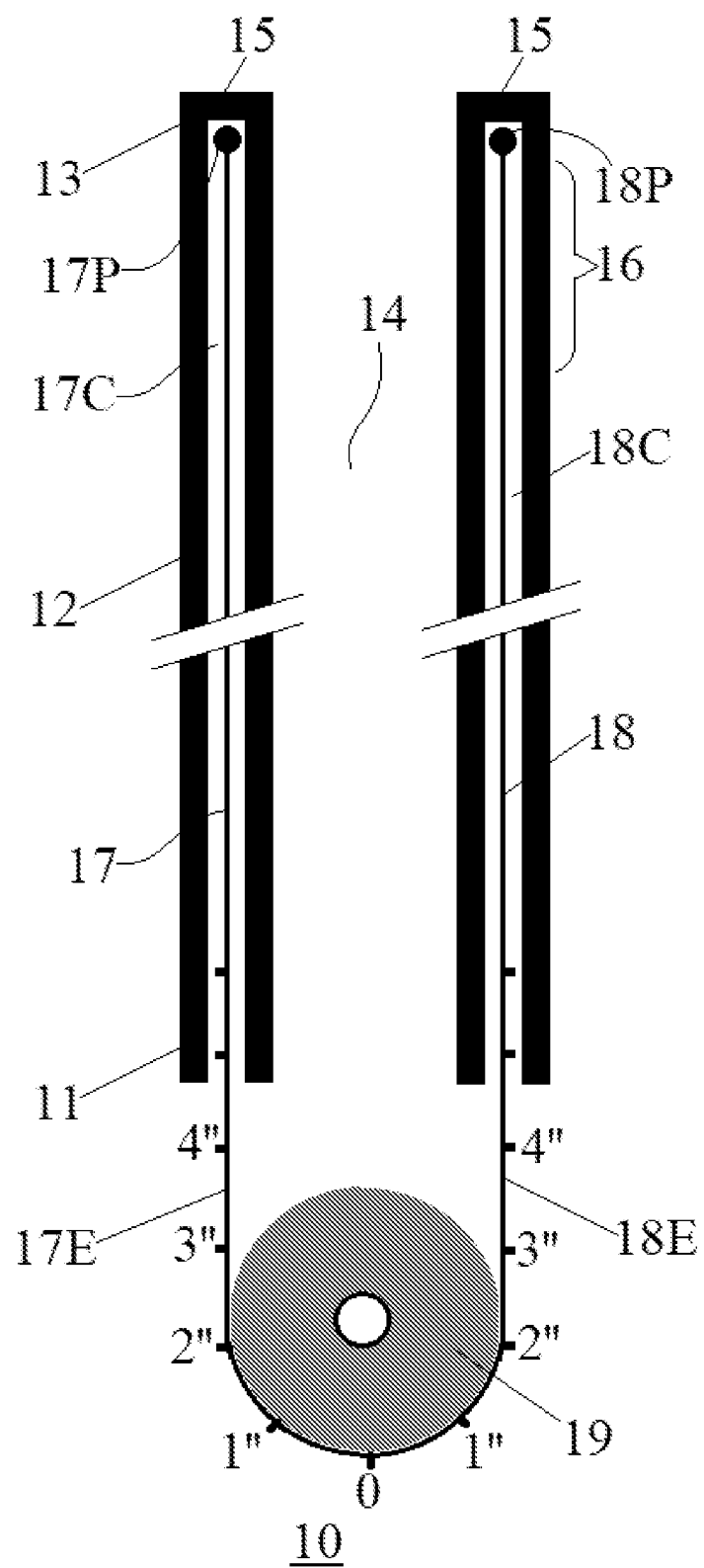
FIG. 1 is a sectional view schematically showing an actively bendable sheath in its natural state in accordance with an exemplary embodiment of the present invention.

With reference to FIG. 1, an actively bendable sheath 10 of the invention is used for delivering a medical instrument (not shown) therethrough. Examples of the medical instrument include, but are not limited to, an endoscope, a hysteroscope, a sigmoidoscope, a bronchoscope, a trocar, a guidewire, and an interventional catheter. The medical instrument may be passively bendable or actively bendable. When the medical instrument is actively bendable, its bending mechanism is different from the bending mechanism of the present invention. In preferred embodiments, actively bendable sheath 10 does not include any functional components of an endoscope, a hysteroscope, a sigmoidoscope, a bronchoscope, a trocar, a guidewire, and an interventional catheter, such as an imaging device e.g. CMOS camera, a surgical tool, and an illuminating device.

Sheath 10 includes a proximal sheath end 11, a distal sheath end 13, and an intermediate sheath region 12 disposed between the proximal sheath end 11 and the distal sheath end 13. A sheath lumen 14 is defined by a tubular wall 15 longitudinally extending from the proximal sheath end 11 to the distal sheath end 13. Sheath lumen 14 may be configured as a passage configured for any suitable medical instrument to pass through it ("delivering"). The tubular wall 15 comprises a deflectable or bendable segment 16 at or adjacent to the distal sheath end 13. The tubular wall 15 at the intermediate sheath region 12 and the proximal sheath end 11 are relatively stiffer than bendable segment 16.

A first pull wire 17 is slidably disposed within a first pull wire channel/lumen 17C that is uniformly or non-uniformly connected to, and extended along, the tubular wall 15 of the sheath 10. A distal end of the first pull wire 17 is affixed to a first attachment point 17P in the first pull wire channel 17C. Likewise, a second pull wire 18 is slidably disposed within a second pull wire channel/lumen 17C that is uniformly or non-uniformly connected to, and extended along, the tubular wall 15 of the sheath 10. A distal end of the second pull wire 18 is affixed to a second attachment point 18P in the second pull wire channel 18C. The first attachment point 17P and the second attachment point 18P are located distally beyond at least a portion of the deflectable segment 16. This portion will be bent during the operation of sheath 10.

In preferred embodiments of the invention, the first pull wire channel 17C is dedicated to the first pull wire 17, the second pull wire channel 18C is dedicated to the second pull wire 18, and both pull wire channels (17C, 18C) are physically separated from the sheath lumen 14. The term "dedicated" means that the channel does not contain any component other than the pull wire 17/18. Except for a terminal "exposed" portion 17E at its proximal end, the first pull wire 17 may be completely confined within the first pull wire channel 17C. Except a portion 18E at its proximal end, the second pull wire 18 may also be completely confined within the second pull wire channel 18C.

As shown in FIG. 1, the first pull wire channel 17C and the second pull wire channel 18C are located within the tubular wall 15 of the sheath 10. However, it should be appreciated that the first pull wire channel 17C and the second pull wire channel 18C may be located onto/into the external surface of the tubular wall 15, or onto/into the internal surface of the tubular wall 15.

Figure 2:
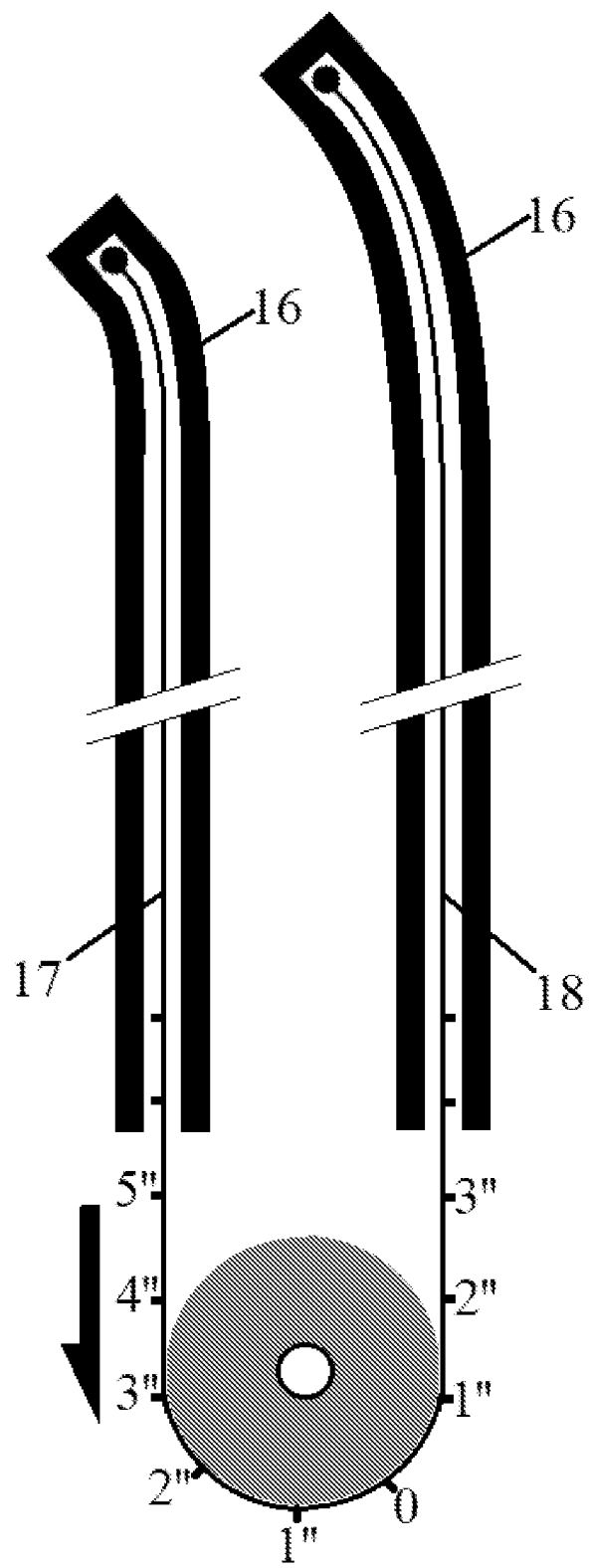
FIG. 2 is a sectional view schematically showing an actively bendable sheath in its "bent left" state in accordance with an exemplary embodiment of the present invention.

As shown in FIG. 2, when the first pull wire 17 is slidably withdrawn by a force (e.g. by a surgeon's hand) from the first pull wire channel 17C, at least a portion of the deflectable segment 16 is bended or deflected toward its side where the first pull wire channel 17C is connected to (i.e. its "right side"). In the meanwhile, the second pull wire 18 will slidably advance or insert into the second pull wire channel 18C.

Figure 3:
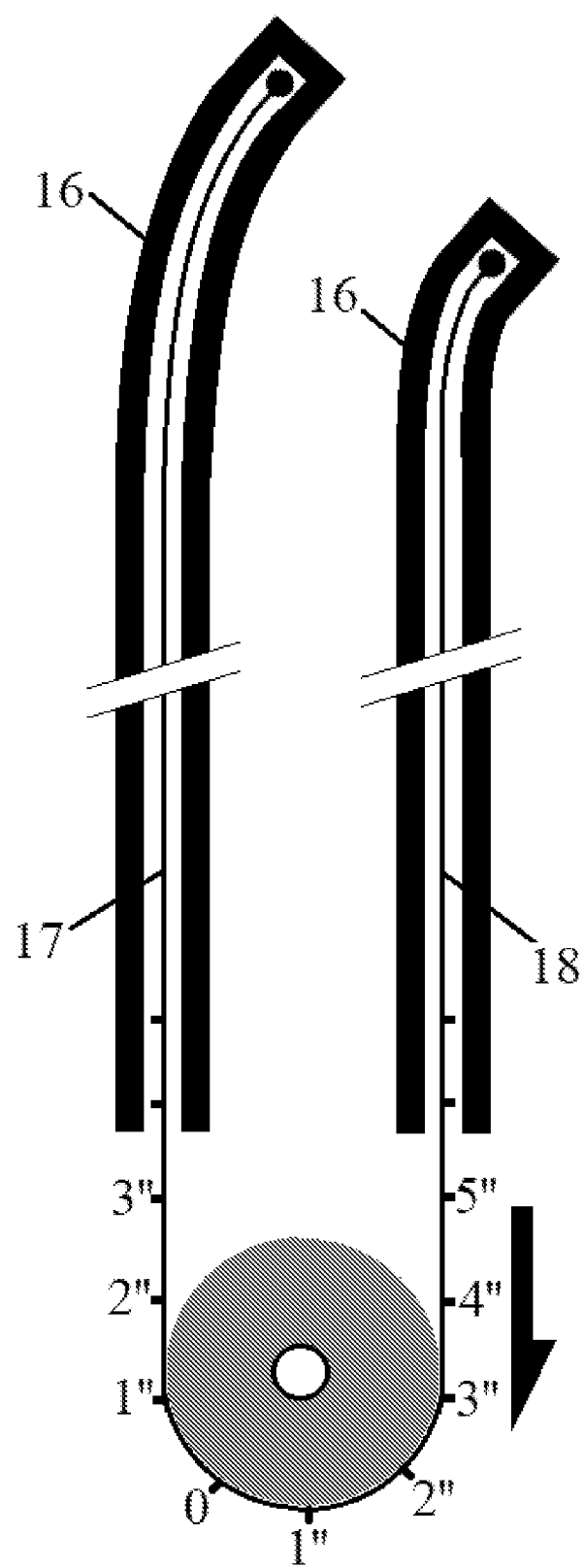
FIG. 3 is a sectional view schematically showing an actively bendable sheath in its "bent right" state in accordance with an exemplary embodiment of the present invention.

As shown in FIG. 3, when the second pull wire 18 is slidably withdrawn by a force (e.g. by a surgeon's hand) from the second pull wire channel 18C, at least a portion of the deflectable segment 16 is bended deflected toward its side where the second pull wire channel 18C is connected to ("left side"). In the meanwhile, the first pull wire 17 will slidably advance or insert into the first pull wire channel 17C.

The first and the second pull wires (17, 18) may be two separated wires, and they are not connected to each other. However, in preferred embodiments a shown in FIGS. 1-3, wires (17, 18) may be connected for form a loop or semi-loop. For example, proximal ends of the first and the second pull wires (17, 18) may be connected forming a continuous wire around a wheel 19. A force that withdraws pull wire 17/18 from its wire channel 17/C/18C may be provided by rotating (e.g. with a surgeon's hand) the wheel 19 clockwise or counterclockwise in a controlled way. In some embodiments, a bendable medical instrument 20 within lumen 14 itself may be actively bended, thereby indirectly bending segment 16. In other words, the bendable segment 16 may be bended accordingly or passively by the force from bending medical instrument 20, rather than from pulling wires (17, 18).

Figure 4:
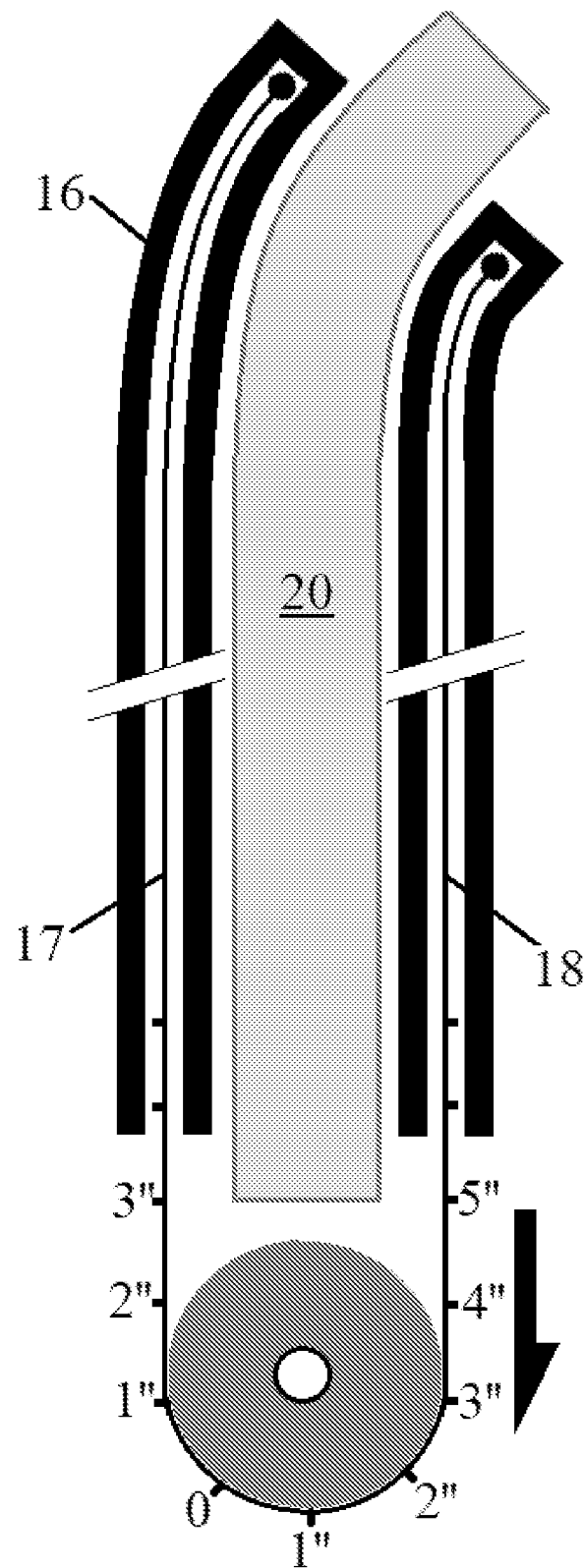
FIG. 4 is a sectional view schematically showing an actively bendable sheath in its "bent right" state delivering a medical instrument in accordance with an exemplary embodiment of the present invention.

The present invention further provides a medical device system as shown in FIG. 4 that includes the actively bendable sheath as described above and illustrated in FIGS. 1-3, and a medical instrument 20, which is either passively or actively bendable. A part of the medical instrument 20 is configured to pass through the sheath 10 or sheath lumen 14, and it will be bended actively or accordingly/passively when it passes through lumen 14 in the deflectable segment 16 (if bent) at or adjacent to the distal sheath end 13.

As shown in FIGS. 1-3, a segment 17E near the proximal end of the first pull wire 17 may be marked at regular intervals (represented as 1", 2", 3", 4" . . . ) to measure a distance that the first pull wire 17 withdraws from or advances into the first pull wire channel 17C. These marks can function as a force meter and a force engagement/disengagement indicator; and they will enable precise controlling the angle of the at least a portion of the deflectable segment 16 being bended toward its side where the first pull wire channel 17C is connected to ("left side"). Similarly, a segment 18E near the proximal end of the second pull wire 18 May also be marked at regular intervals (represented as 1", 2", 3", 4" . . . ) to measure a distance that the second pull wire 18 withdraws from or advances into the second pull wire channel 18C. These marks will enable precise controlling the angle of the at least a portion of the deflectable segment 16 being bended toward its side where the second pull wire channel 18C is connected to ("right side").

Figure 5:
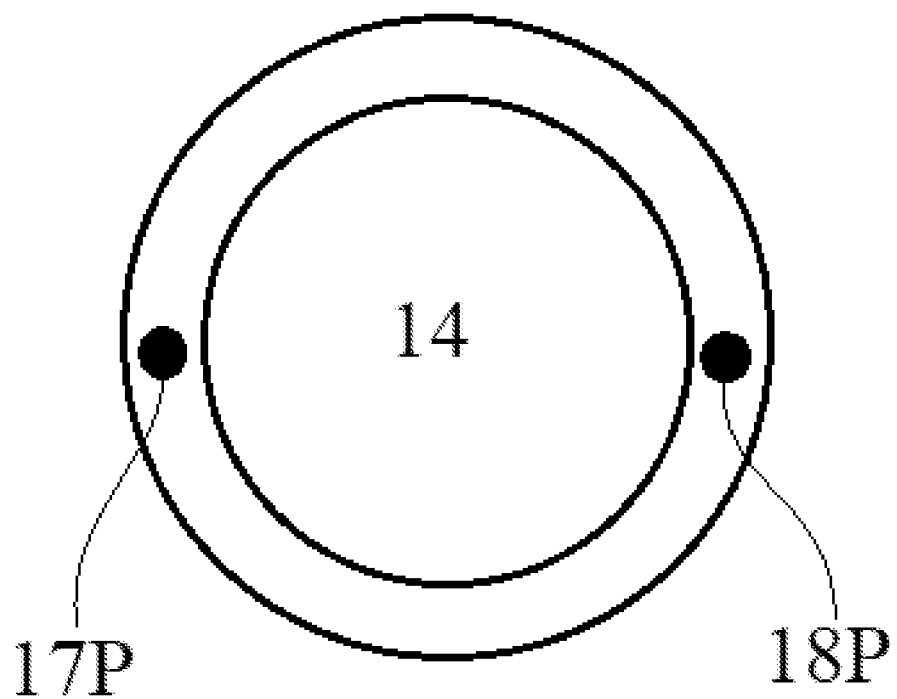
FIG. 5 is a sectional view of two attachment points for affixing two pull/control wires in an actively bendable sheath in accordance with an exemplary embodiment of the present invention.

In preferred embodiments as shown in FIG. 5, the first attachment point 17P and the second attachment point 18P are 180-degree opposite to each other across the sheath lumen 14. In other words, two points (17P, 18P) and a point in the longitudinal axis of the sheath lumen 14 are aligned along a substantially straight line.

Figure 6:
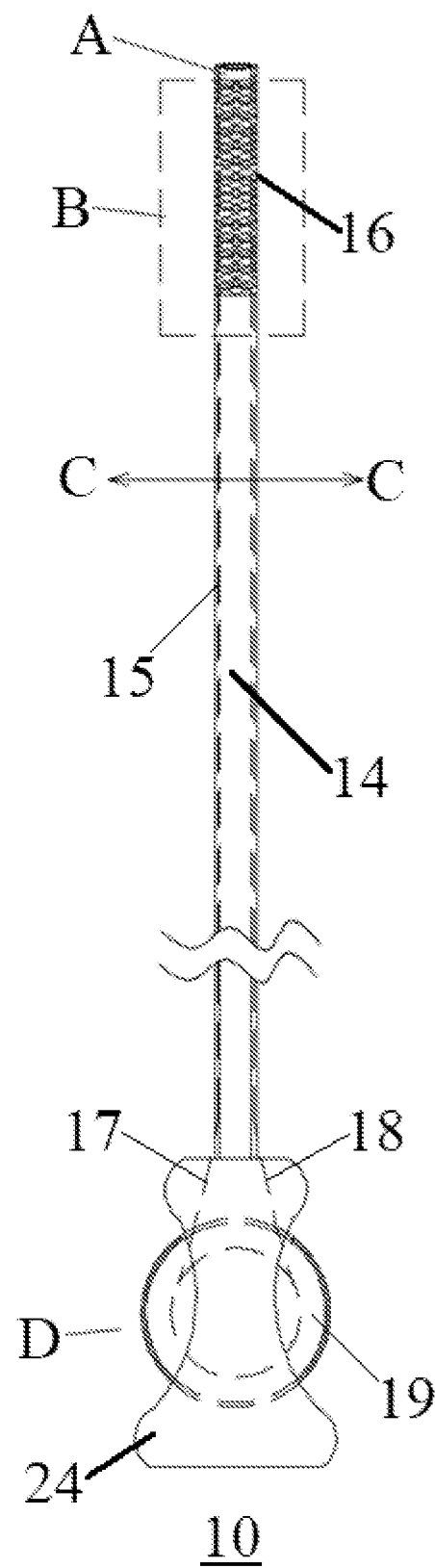
FIG. 6 illustrates a ureteral access sheath in accordance with an exemplary embodiment of the present invention.

FIG. 6 illustrates an exemplary embodiment of the sheath 10 such as an access sheath with a first pull wire or control wire 17 and a second pull wire or control wire 18, both of which may be made of steel. Sheath 10 includes at least three sections A, B and D; and a cross sectional line C-C between section B and section D, which will be described in more details. The access sheath 10 may be used for delivering a medical instrument (not shown) therethrough. Sheath lumen 14 is configured for any medical instrument to pass through it ("delivering"). The tubular wall 15 comprises a deflectable or bendable segment 16. A handle 24 equipped with a deflection wheel 19 may be installed/disposed at, and operably linked to, the proximal sheath end. Handle 24 may provide access into sheath lumen 14.

Figure 7:
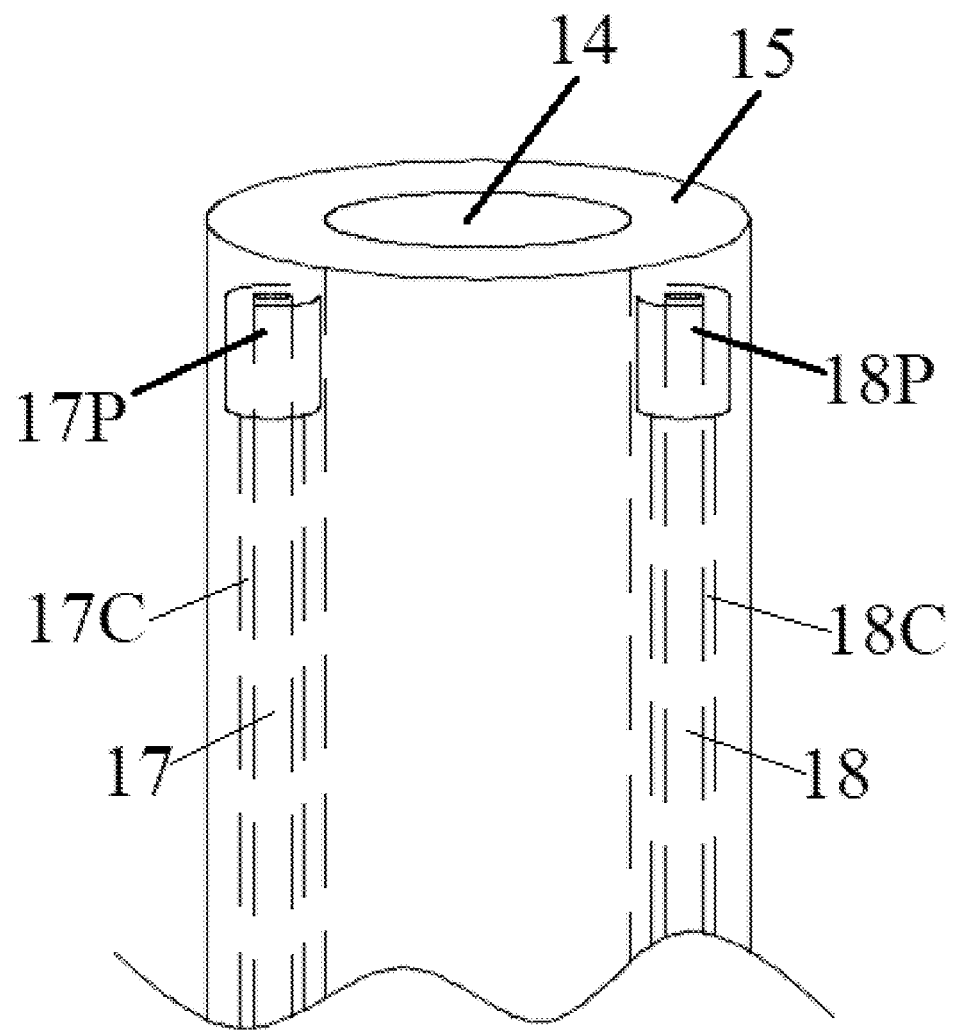
FIG. 7 illustrates the distal end structure of the ureteral access sheath of FIG. 6 in accordance with an exemplary embodiment of the present invention.

FIG. 7 shows section A of the access sheath 10 in FIG. 6. A first pull wire or control wire 17 is slidably disposed within a first pull wire channel/lumen 17C that is connected to, and extended along, the tubular wall 15 of the sheath 10. A second pull wire or control wire 18 is slidably disposed within a second pull wire channel/lumen 18C that is connected to, and extended along, the tubular wall 15 of the sheath 10. A distal end of the first pull wire 17 is affixed to a first steel wire ferrule 17P in the first pull wire channel 17C. A distal end of the second pull wire 18 is affixed to a second steel wire ferrule 18P in the second pull wire channel 18C. The first attachment point 17P and the second attachment point 18P are located distally beyond the entire deflectable segment 16.

Figure 8:
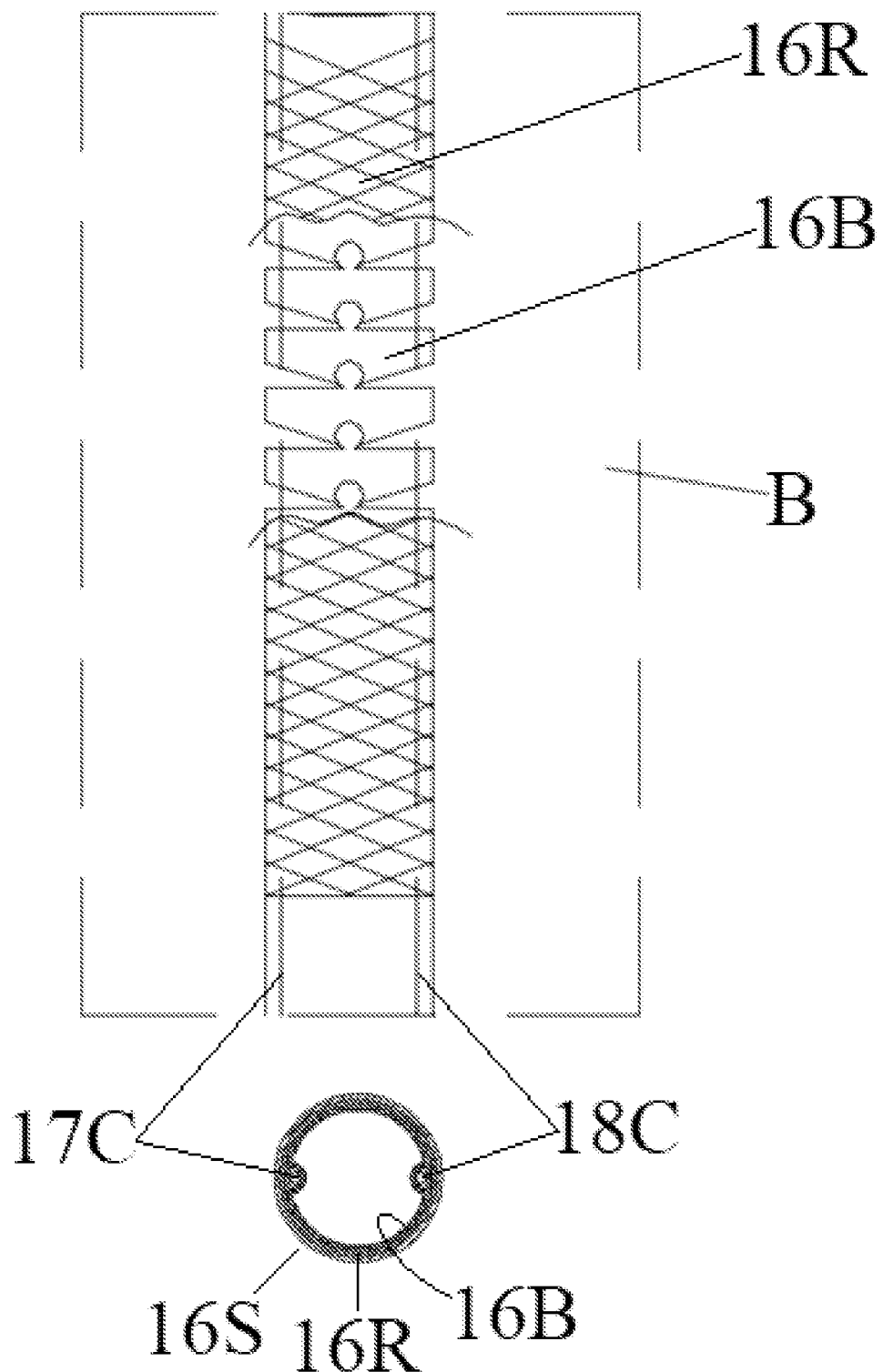
FIG. 8 illustrates the deflectable segment structure of the ureteral access sheath of FIG. 6 in accordance with an exemplary embodiment of the present invention.

FIG. 8 shows section B of the access sheath 10 in FIG. 6. The tubular wall 15 of deflectable segment 16 includes 3 layers: a braiding layer 16R sandwiched between a rubber sleeve 16S and actively bendable "snake bones" 16B. The first pull wire channel 17C and the second pull wire channel 18C are located onto/into the internal surface of the tubular wall 15.

Figure 9:
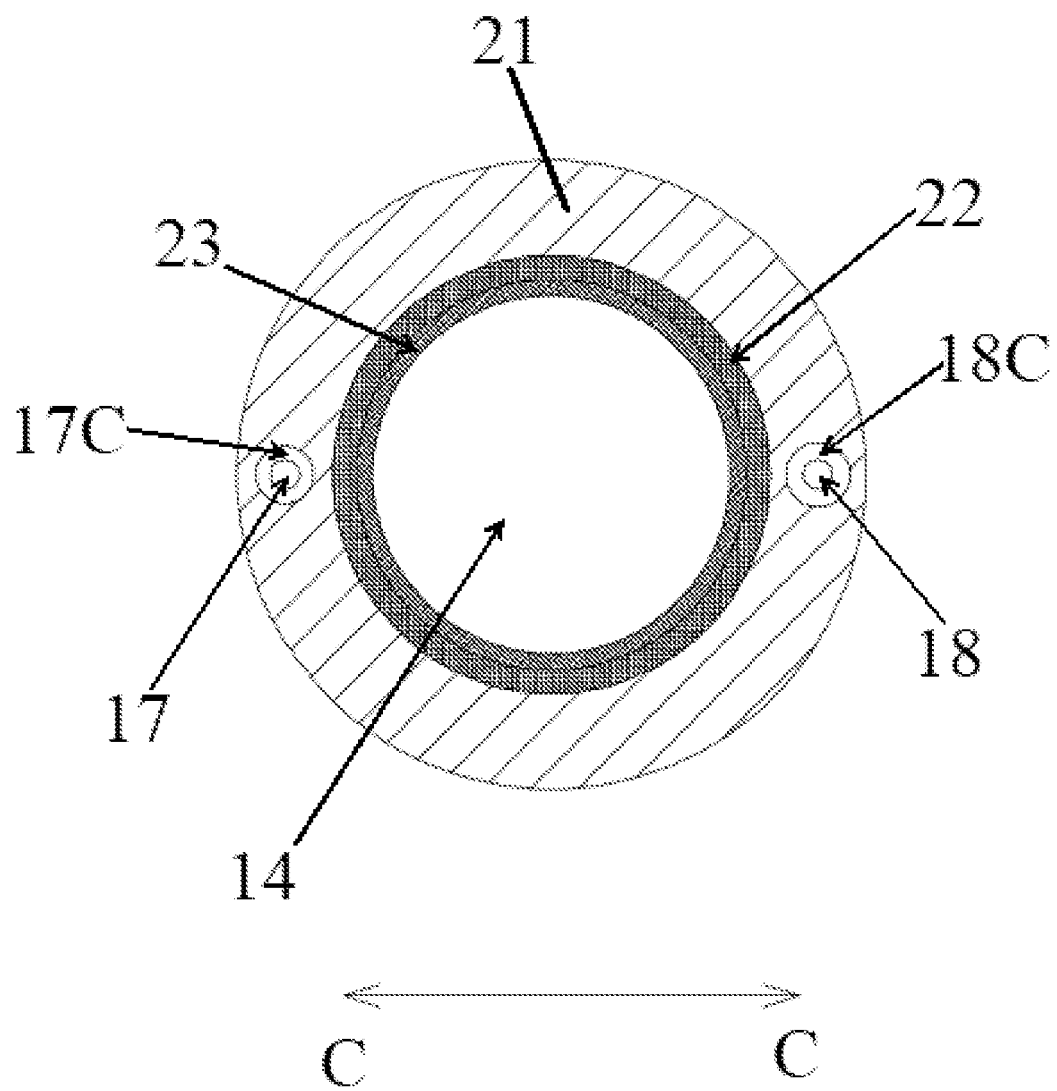
FIG. 9 is a sectional view showing the intermediate sheath region of the ureteral access sheath of FIG. 6 in accordance with an exemplary embodiment of the present invention.

FIG. 9 shows the cross-sectional view along C-C of the access sheath 10 in FIG. 6. The tubular wall 15 here includes 3 layers: a stainless-steel mesh layer 22 sandwiched between a polymeric cover layer 21 and a spring tube layer 23. Cover 21 provides a smooth and low friction outer surface. For example, the tubular wall 15 may consist of a polytetrafluoroethylene (PTFE) inner liner surrounded by a steel coil reinforcement layer surrounded by a polymer jacket. Additionally, the first pull wire channel 17C and the second pull wire channel 18C are located within the tubular wall 15.

As shown in FIGS. 7 and 9, the first pull wire channel 17C and the second pull wire channel 18C are generally located within the tubular wall 15 of the sheath 10. However, in the bendable segment 16 as shown in FIG. 8, they may be located onto/into the internal surface of the tubular wall 15.

Figure 10A:
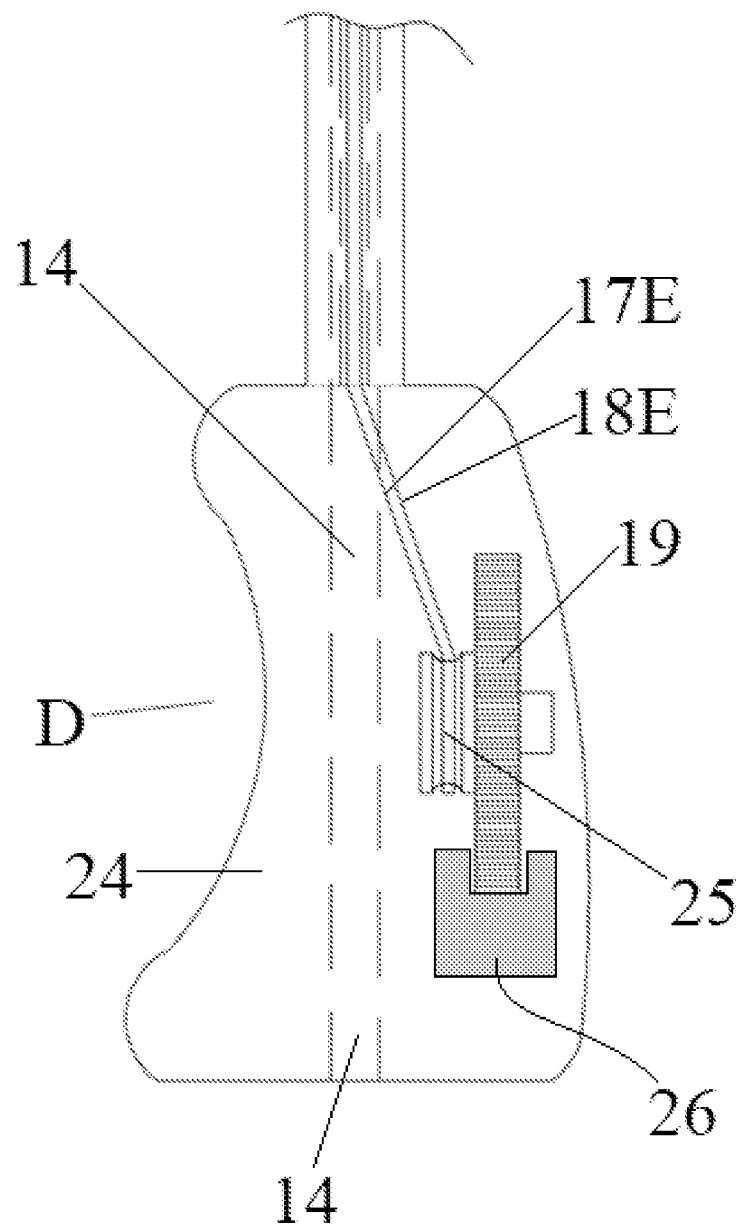
FIG. 10A illustrates a view of the proximal end structure of the ureteral access sheath of FIG. 6 in accordance with an exemplary embodiment of the present invention.
Figure 10B:
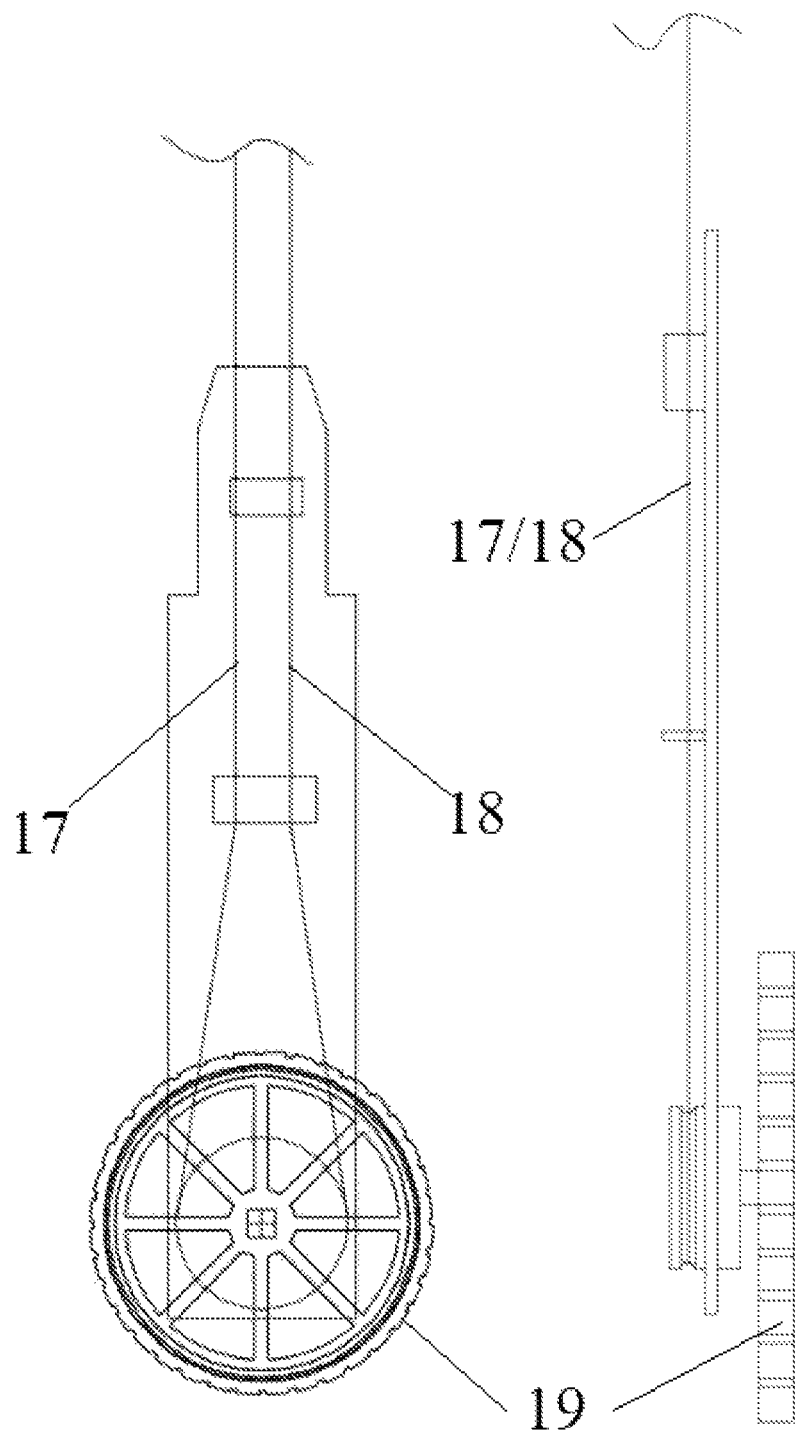
FIG. 10B illustrates other views of the proximal end structure of the ureteral access sheath of FIG. 6 in accordance with an exemplary embodiment of the present invention.

FIG. 10A shows section D of the access sheath 10 in FIG. 6. The proximal sheath end may be installed/disposed with, and operably linked to, a handle 24 equipped with a deflection wheel 19 including a grooved rim 25 around which a continuous wire (17 and 18 being connected) passes. As shown in FIG. 10A, the first pull wire channel 17C is dedicated to the first pull wire 17, the second pull wire channel 18C is dedicated to the second pull wire 18, and both pull wire channels (17C, 18C) are separated from the sheath lumen 14. Except for a terminal portion 17E exposed at its proximal end, the first pull wire 17 may be completely confined within the first pull wire channel 17C. Except a portion 18E at its proximal end, the second pull wire 18 may be completely confined within the second pull wire channel 18C. The deflection wheel 19 may work with a locking element or a brake 26 which is configured to stop rotating the defection wheel 19 when the deflectable segment 16 is bent with a predetermined or desirable angle. For example, the brake 26 may be a part of the handle's case or shell that gently touches wheel 19 which is made of elastic material and generates a suitable friction between the two. When a surgeon steers or bends the sheath 10 by rotating wheel 19 with his finger(s), e.g. clockwise, the force from the surgeon's finger(s) can overcome the friction. When the surgeon's finger(s) does not touch wheel 19 anymore, the friction is strong enough to prevent wheel 19 rotate back, e.g. counterclockwise. FIG. 10B shows other two views of the wheel 19 and pull wires 17 and 18.

Figure 11:
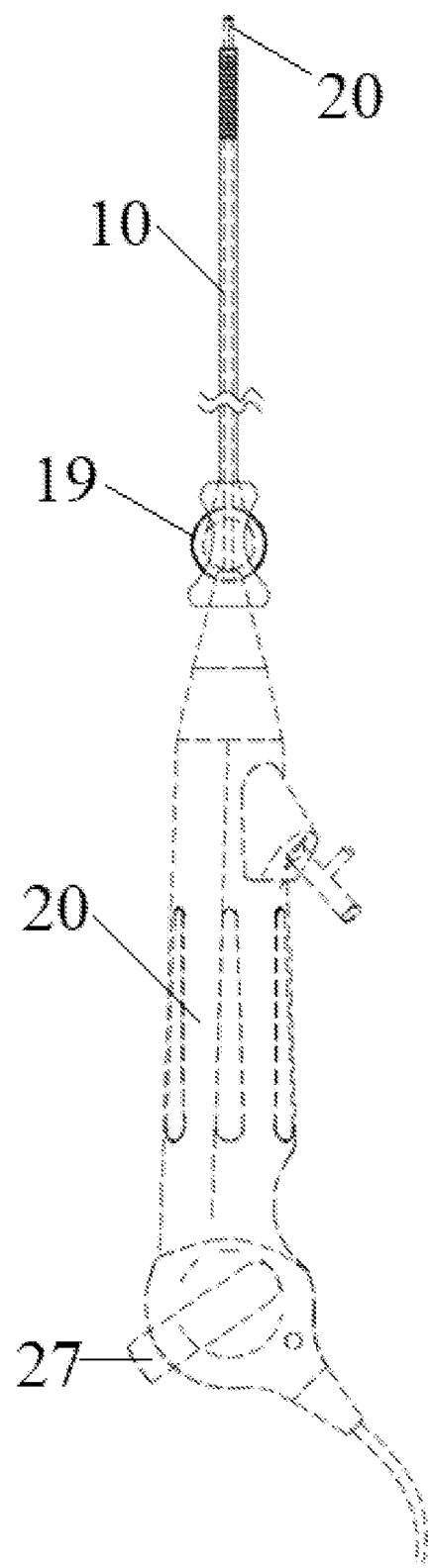
FIG. 11 illustrates a ureteroscope within the ureteral access sheath of FIG. 6 in its natural state in accordance with an exemplary embodiment of the present invention.

The present invention further provides a medical device system as shown in FIG. 11 that includes the actively bendable sheath as described above and illustrated in FIGS. 6-10B, and a medical instrument 20. At least a part of the medical instrument 20 is configured to pass through the sheath 10 or sheath lumen 14, and it will be bended actively or passively when it passes through lumen 14 in the deflectable segment 16 (if bent) at or adjacent to the distal sheath end 13. The medical instrument 20 may be free of any pull wires or control wires (like wires 17 and 18) and the pull wire channels (17C and 18C) as defined above. Examples of the medical instrument 20 may include, but not limited to, an endoscope, a trocar, a guidewire, an interventional catheter, and an ureteroscope.

For example, an endoscope may be inserted into the patient through the sheath 10 such as a UAS of the invention, desirably using a body passageway, such as a ureter or a blood vessel. An endoscope includes an integral optical system, a working channel, and a way to maneuver the endoscope so that the surgeon can accomplish a therapeutic or diagnostic procedure. The surgeon positions the endoscope so that the surgeon can observe the desired body part of the patient using the optical system, with irrigation if necessary. The surgeon then uses at least one instrument, such as a laser or a grasper, to break up and remove objects in the body passageway. The endoscope may also be used for diagnostic purposes, such as for observing the desired portion of the patient and then taking a biopsy sample.

For ureteral use, the overall length of the ureteral access sheath can be, for example, from 20 cm to 55 cm, with the outer diameter being less than 16 Fr (1 Fr=0.0135 inch). These dimensions are approximate, and in practical terms, depend upon sizes suitable for a particular purpose. The ureteral access sheath of the invention may be placed into a ureter before retrograde flexible ureteroscopy to provide a working channel to the ureter for a flexible ureteroscope and to provide real-time drainage of lavage fluid to maintain a clear view field and to reduce intrapelvic pressure.

The ureteral access sheaths of the invention may be used to gain access to body cavities in lumens during endoscopic and laparoscopic surgery, and by other procedures that generally use minimally invasive techniques. Thus, the ureteral access sheaths may be used with an endoscope for finding and removing kidney stones, and may be used in other applications, such as access to bile ducts. After the endoscope is removed, the sheath 10 such as a UAS of the invention may suck the stone pieces away, using a vacuum pump (not shown).

Other applications for which an access sheath has been used include vascular procedures, as well as procedures requiring gastro-intestinal access, uterine access, and bronchial access. Thus, sheaths of the invention may be used in combination with endoscopes, hysteroscopes, sigmoidoscopes, bronchoscopes, and many other types of instruments for minimally invasive techniques.

For instance, typical kidney stone retrieval procedures require multiple insertions and removals of the stone basket and endoscope as successive stone fragments are captured. The access sheath of the invention protects the ureter from sharp points or jagged edges of the stone fragments as they are pulled from the ureter or kidney. The access sheath also provides the physician with an established pathway into the ureter avoiding the need to re-establish that path from the urethra through the bladder and into the ureter for each insertion of the endoscope.

Figure 14:
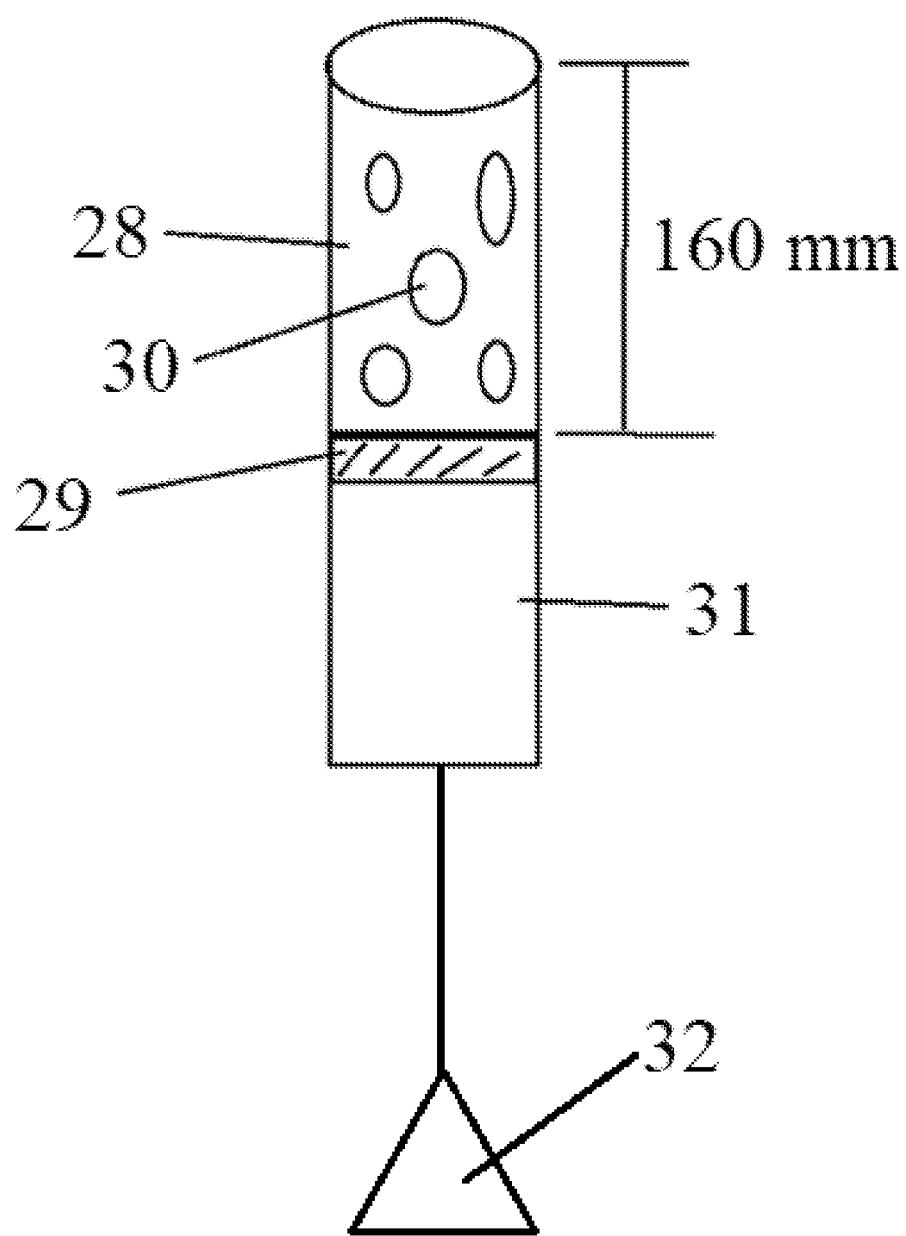
FIG. 14 illustrates the distal sheath end structure of a ureteral access sheath in accordance with an exemplary embodiment of the present invention.

In an embodiment as shown in FIG. 14, the distal sheath end 13 structure of a ureteral access sheath 10 may include a soft and bendable portion 28 (with memory-setting to keep at the desired bending position, similar to the auto-lock function), a joint 29 below portion 28, and stiff portion 31 below joint 29. Openings 30 in portion 28 may be used for fluid/stones flowing (with e.g. sizes 1-1.2 mm; 2 holes total—one on each side; or more than 2 holes distributed across portion 28), facilitated by a vacuum source 32 such as a vacuum pump.

Figure 12:
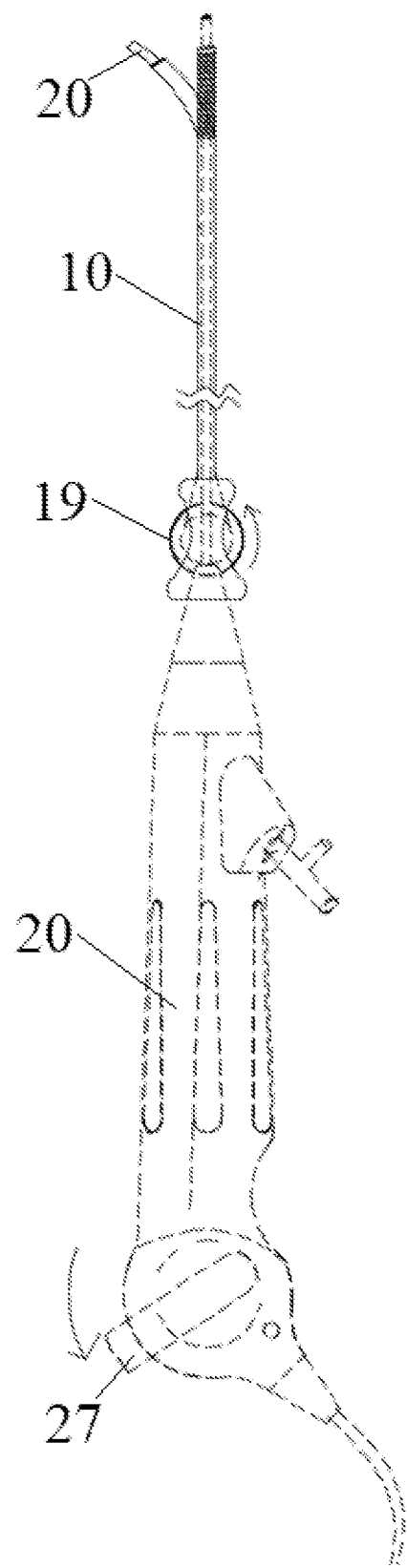
FIG. 12 illustrates a ureteroscope within the ureteral access sheath of FIG. 6 in its "bent left" state in accordance with an exemplary embodiment of the present invention.

As shown in FIG. 12, when the first pull wire 17 is slidably withdrawn by force from the first pull wire channel 17C, at least a portion of the deflectable segment 16 is bended or deflected toward its side where the first pull wire channel 17C is connected to ("right side"). In the meanwhile, the second pull wire 18 will slidably advance or insert into the second pull wire channel 18C.

Figure 13:
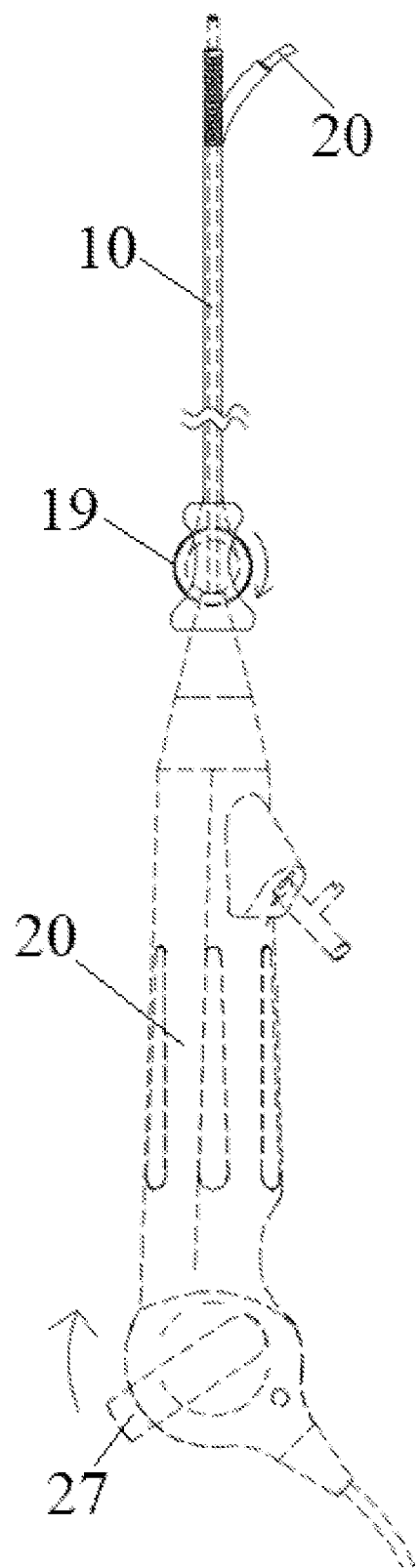
FIG. 13 illustrates a ureteroscope within the ureteral access sheath of FIG. 6 in its "bent right" state in accordance with an exemplary embodiment of the present invention.

As shown in FIG. 13, when the second pull wire 18 is slidably withdrawn by force from the second pull wire channel 18C, at least a portion of the deflectable segment 16 is bended deflected toward its side where the second pull wire channel 18C is connected to ("left side"). In the meanwhile, the first pull wire 17 will slidably advance or insert into the first pull wire channel 17C.

As shown in FIGS. 11-13, the first and the second pull wires (17, 18) are connected. For example, proximal ends of the first and the second pull wires (17, 18) are connected forming a continuous wire around a wheel 19. A force that withdraws pull wire 17/18 from its wire channel 17/C/18C may be provided by rotating the wheel clockwise or counterclockwise in a controlled way.

As shown in FIG. 11, an endoscope 20 has been inserted into sheath 10. When a direction controller 27 in the endoscope 20 is rotated anticlockwise, the sheath 10 will be forced to bend anticlockwise, as shown in FIG. 12. When no endoscope is inserted into sheath 10, the sheath 10 can still be bent anticlockwise by rotating wheel 19 anticlockwise. If the rotating wheel 19 is locked and prevented from rotating further either anticlockwise or clockwise, then the bending degree of the sheath 10 may be maintained after the wheel 19 is released from control.

When the direction controller 27 in the endoscope 20 is rotated clockwise, the sheath 10 will be forced to bend clockwise, as shown in FIG. 13. When no endoscope is inserted into sheath 10, the sheath 10 can still be bent clockwise by rotating wheel 19 clockwise. If the rotating wheel 19 is locked and prevented from rotating further either anticlockwise or clockwise, then the bending degree of the sheath 10 may be maintained after the wheel 19 is released from control.

The present invention further provides a method of using the actively bendable sheath as described above. In preferred embodiments, active deflection of segment 16 may be directed by an intraluminal endoscope. Endoscopy guidance does not need a fluoroscopy confirmation. Segment 16 may have auto memory in deflection angle after the ureteroscope is removed. Reduction of lumen 14 is minimal with active deflection. Transparent lumen may be designed at the distal tip, with side holes for optimizing stone fragment suction. Lumen 14 may have routine deflection up to 120 degrees (e.g. 100-120 degrees). The sheath size (ID/OD) may be 10/12 Fr or 12/14 Fr; and the sheath length may be 35 cm, 45 cm or 55 cm. Advantageously, the UAS of the invention may be a dual-durometer sheath that allows the ideal flexibility to navigate tortuously to reach to renal calyces. The tip can deflect with the WiScope® single use ureteroscope and retrieval devices inserted. A built-in memory-setting (auto-lock or brake 26 as shown in FIG. 10A) keeps the UAS at the ideal bending position. Side-holes or openings can increase flow and vacuum of fluid/stones, and they may have sizes of 1-1.2 mm (2 holes total, one on each side of segment 16).

Figure 15:
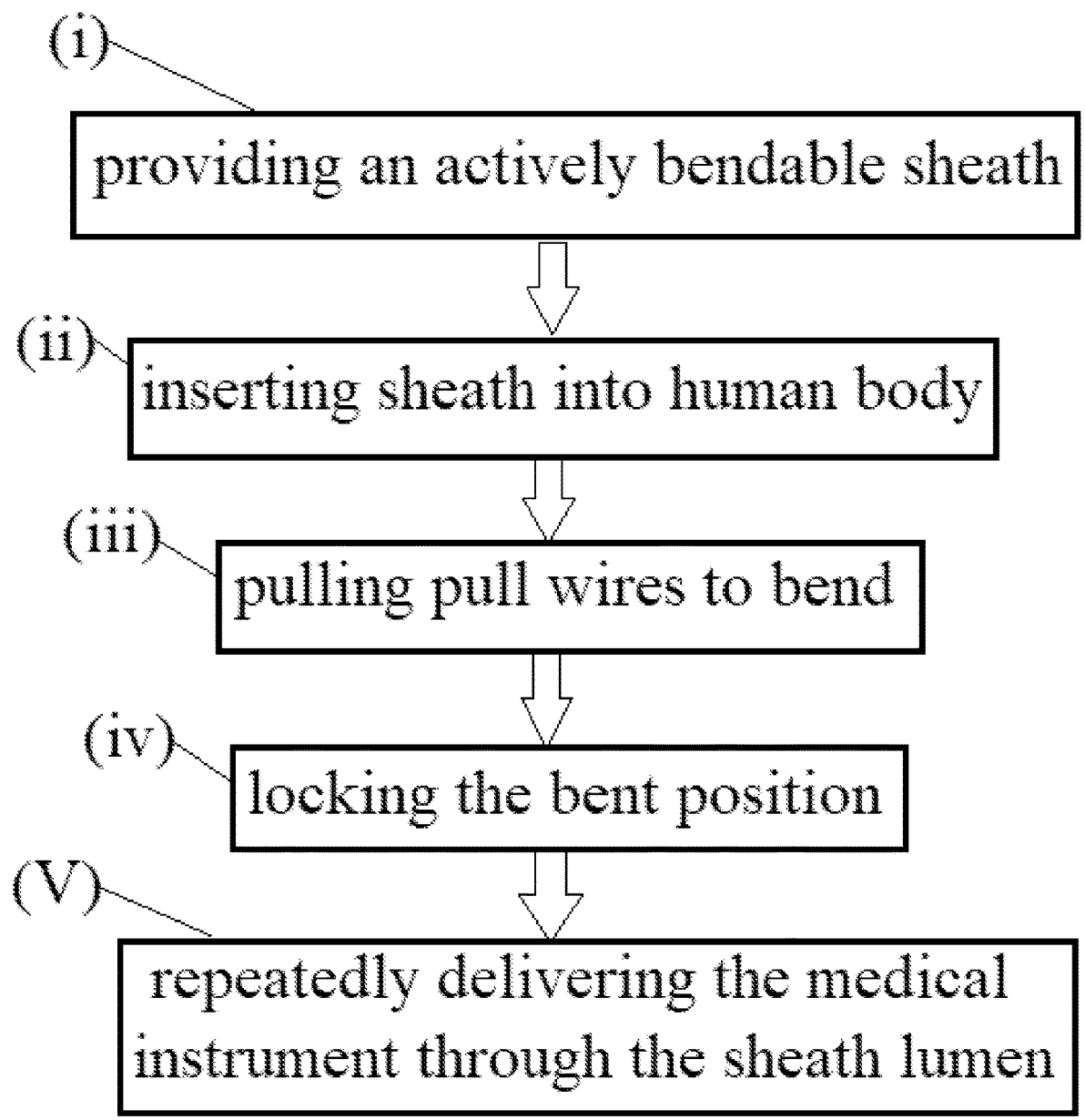
FIG. 15 is the flow chart of a method for delivering a medical instrument into human body through a ureteral access sheath in accordance with an exemplary embodiment of the present invention.

As shown in FIG. 15, the present invention provides a method for delivering a medical instrument into human body through the sheath (e.g. a ureteral access sheath) as described above. The method includes:

(i) providing an actively bendable sheath comprising a proximal sheath end; a distal sheath end; an intermediate sheath region disposed between the proximal sheath end and the distal sheath end; a sheath lumen defined by a tubular wall extending from the proximal sheath end to the distal sheath end, and configured for the medical instrument to pass through it ("delivering"), the tubular wall comprising a deflectable or bendable segment at or adjacent to the distal sheath end; a first pull wire slidably disposed within a first pull wire channel/lumen that is connected to, and extended along, the tubular wall of the sheath, wherein a distal end of the first pull wire is affixed to a first attachment point in the first pull wire channel; and a second pull wire slidably disposed within a second pull wire channel/lumen that is connected to, and extended along, the tubular wall of the sheath, wherein a distal end of the second pull wire is affixed to a second attachment point in the second pull wire channel; wherein the first attachment point and the second attachment point are located distally beyond at least a portion of the deflectable segment;

(ii) inserting the actively bendable sheath into human body;

(iii) pulling the first pull wire or the first pull wire to bend the deflectable segment;

(iv) locking the deflectable segment at the bent position; and (v) repeatedly delivering the medical instrument through the sheath lumen.

The method may further include a step of providing a wheel 19 as described above and accomplishing step (iii) by rotating wheel 19 clockwise or counterclockwise.

Technical advantages of the invention (particularly the UAS) include the following: Active deflection directed by an intraluminal endoscope; Endoscopy guidance with no need for a fluoroscopy confirmation; Auto memory in deflection angle after the ureteroscope is removed; Minimal lumen reduction with active deflection; Transparent lumen at the distal tip; Side holes 30 for optimizing stone fragment suction; Routine deflection up to 120 degrees; 2-way deflections; a dual-durometer sheath allows the ideal flexibility to navigate tortuously to reach to renal calyces; the tip can deflect with the WiScope® single-use ureteroscope and retrieval devices inserted; a built-in memory-setting (auto-lock) keeps the UAS at the ideal bending position; and side-holes 30 increase flow and vacuum of fluid/stones.

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. An actively bendable sheath used for delivering an endoscope or an ureteroscope that is not part of the sheath, comprising:

a proximal sheath end;

a distal sheath end;

an intermediate sheath region disposed between the proximal sheath end and the distal sheath end;

only one sheath lumen defined by a tubular wall extending from the proximal sheath end to the distal sheath end, and configured for the endoscope or the ureteroscope to pass through it, the tubular wall comprising a deflectable or bendable segment at or adjacent to the distal sheath end; and only two pull wires including a first pull wire slidably disposed within a first pull wire channel/lumen that is connected to, and extended along, the tubular wall of the sheath, wherein a distal end of the first pull wire is affixed to a first attachment point in the first pull wire channel; and a second pull wire slidably disposed within a second pull wire channel/lumen that is connected to, and extended along, the tubular wall of the sheath, wherein a distal end of the second pull wire is affixed to a second attachment point in the second pull wire channel;

wherein the first attachment point and the second attachment point are located distally beyond at least a portion of the deflectable segment, wherein the actively bendable sheath itself does not include an imaging device, a CMOS camera, a surgical tool, or an illuminating device as functional components of an endoscope, a hysteroscope, a sigmoidoscope, a bronchoscope, a trocar, a guidewire, and an interventional catheter, wherein the first pull wire channel and the second pull wire channel are located onto and therefore protruded out from the internal surface of the tubular wall of said deflectable or bendable segment, but they are located within and therefore buried into a tubular wall proximally to said deflectable or bendable segment, and wherein the distal sheath end includes a soft and bendable portion as said deflectable or bendable segment, and wherein said soft and bendable portion has more than 2 holds of size 1-1.2 mm for kidney stones to flow through.

2. The actively bendable sheath according to claim 1,
wherein the tubular wall of said deflectable or bendable segment consists of 3 layers: a braiding layer sandwiched between a rubber sleeve and actively bendable "snake bones"; and wherein a tubular wall proximally to said deflectable or bendable segment consists of 3 layers: a stainless-steel mesh later sandwiched between a polymeric cover layer and a spring tube layer.

3. The actively bendable sheath according to claim 1, wherein, when the first pull wire is slidably withdrawn by force from the first pull wire channel, said at least a portion of the deflectable segment is bended toward its side where the first pull wire channel is connected to; and wherein, when the first pull wire is slidably withdrawn by force from the first pull wire channel, the second pull wire slidably advances into the second pull wire channel.

4. The actively bendable sheath according to claim 1, wherein, when the second pull wire is slidably withdrawn by force from the second pull wire channel, said at least a portion of the deflectable segment is bended toward its side where the second pull wire channel is connected to; and wherein, when the second pull wire is slidably withdrawn by force from the second pull wire channel, the first pull wire slidably advances into the first pull wire channel.

5. The actively bendable sheath according to claim 1, wherein the first pull wire channel is dedicated to the first pull wire, the second pull wire channel is dedicated to the second pull wire, and both pull wire channels are separated from the sheath lumen.

6. The actively bendable sheath according to claim 1, wherein, except for a portion at its proximal end, the first pull wire is completely confined within the first pull wire channel; and wherein, except for a portion at its proximal end, the second pull wire is completely confined within the second pull wire channel.

7. The actively bendable sheath according to claim 1, wherein the first attachment point and the second attachment point are opposite to each other across the sheath lumen.

8. The actively bendable sheath according to claim 1, wherein proximal ends of the first and the second pull wire are connected forming a continuous wire, and wherein the proximal sheath end further includes a handle equipped with a deflection wheel including a grooved rim around which a continuous wire passes.

9. The actively bendable sheath according to claim 8, wherein the deflection wheel is rotatable, and wherein the sheath includes a locking element configured to stop rotating of the deflection wheel when the deflectable segment is bended to a predetermined or desirable angle.

10. The actively bendable sheath according to claim 1, wherein a segment near the proximal end of the first pull wire is marked at regular intervals to measure a distance that the first pull wire withdraws from or advances into the first pull wire channel, and thereby control the angle of said at least a portion of the deflectable segment being bended toward its side where the first pull wire channel is connected to.

11. The actively bendable sheath according to claim 1, wherein a segment near the proximal end of the second pull wire is marked at regular intervals to measure a distance that the second pull wire withdraws from or advances into the second pull wire channel, and thereby control the angle of said at least a portion of the deflectable segment being bended toward its side where the second pull wire channel is connected to.

12. A medical device system comprising an actively bendable sheath of claim 1 and an endoscope or an ureteroscope configured to pass through the sheath, and to be bended passively when it passes through the deflectable segment at or adjacent to the distal sheath end, wherein the endoscope or the ureteroscope is free of pull wire.

13. The medical device system according to claim 12,
wherein the tubular wall of said deflectable or bendable segment consists of 3 layers: a braiding layer sandwiched between a rubber sleeve and actively bendable "snake bones"; and wherein a tubular wall proximally to deflectable or bendable segment consists of 3 layers: a stainless-steel mesh layer sandwiched between a polymeric cover layer and a spring tube layer.

14. The medical device system according to claim 12, wherein proximal ends of the first and the second pull wire are connected forming a continuous wire, and wherein the proximal sheath end further includes a deflection wheel with a grooved rim around which a continuous wire passes.

15. The medical device system according to claim 14, wherein the deflection wheel is rotatable, and wherein the sheath includes a locking element configured to stop rotating of the deflection wheel when the deflectable segment is bended to a predetermined or desirable angle.

16. The medical device system according to claim 12, wherein a segment near the proximal end of the first pull wire is marked at regular intervals to measure a distance that the first pull wire withdraws from or advances into the first pull wire channel, and thereby control the angle of said at least a portion of the deflectable segment being bended toward its side where the first pull wire channel is connected to.

17. The medical device system according to claim 12, wherein a segment near the proximal end of the second pull wire is marked at regular intervals to measure a distance that the second pull wire withdraws from or advances into the second pull wire channel, and thereby control the angle of said at least a portion of the deflectable segment being bended toward its side where the second pull wire channel is connected to.

18. A method for delivering an endoscope or an ureteroscope into human body, comprising
(i) providing an actively bendable sheath of claim 1;
(iii) pulling the first pull wire or the second pull wire to bend the deflectable segment;
(iv) locking the deflectable segment at the bent position; and
(v) repeatedly delivering the endoscope or the ureteroscope through the sheath lumen.

* * * * *